(12) United States Patent
Sakano et al.

(10) Patent No.: US 7,102,032 B2
(45) Date of Patent: Sep. 5, 2006

(54) PURIFICATION OF AMIDE COMPOUND

(75) Inventors: Yasunori Sakano, Usui-gun (JP); Noriyuki Koike, Usui-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/828,245

(22) Filed: Apr. 21, 2004

(65) Prior Publication Data

US 2004/0215037 A1 Oct. 28, 2004

(30) Foreign Application Priority Data

Apr. 24, 2003 (JP) .............................. 2003-119375

(51) Int. Cl.
*C07C 209/84* (2006.01)
(52) U.S. Cl. .................. 564/4; 564/135; 564/137; 564/153; 556/419
(58) Field of Classification Search ................ 564/135, 564/137, 4, 153; 556/419
See application file for complete search history.

(56) References Cited

U.S. PATENT DOCUMENTS 2,713,593 A * 7/1955 Brice et al. ................. 562/586
3,743,704 A * 7/1973 West .......................... 423/490

FOREIGN PATENT DOCUMENTS

| DE | 26 01 375 | * | 7/1977 |
| EP | 0 709 366 | * | 5/1996 |
| JP | 8-127560 |   | 5/1996 |

* cited by examiner

*Primary Examiner*—Shailendra Kumar
(74) *Attorney, Agent, or Firm*—Oblon, Spivak, McClelland, Maier & Neustadt, P.C.

(57) ABSTRACT

In the synthesis of an amide compound through reaction of an acyl fluoride group-bearing compound with an amino compound, a reaction mixture contains the amide compound and hydrogen fluoride or a hydrofluoric acid amine salt. The amide compound is recovered in high purity form by adding an oxide, carbonate or hydroxide of an alkaline earth metal to the reaction mixture to convert the hydrogen fluoride or hydrofluoric acid amine salt to an alkaline earth metal fluoride salt that can be readily removed by filtration.

16 Claims, No Drawings

PURIFICATION OF AMIDE COMPOUND

FIELD OF THE INVENTION

This invention relates to a method for purifying an amide compound, and more particularly, to a simple purifying method of recovering a target amide compound at a high purity in a high yield from a reaction mixture resulting from reaction of an acyl fluoride group-bearing compound with an amino compound.

BACKGROUND ART

In the prior art, an amide compound is synthesized from a compound having an acyl fluoride group within a molecule through several routes, for example, by direct reaction of the acyl fluoride group-bearing compound with an amino compound. It is known that this direct reaction proceeds in a quantitative manner. During the reaction, hydrogen fluoride is produced as a by-product. If the amino compound is present in excess in the reaction system, hydrogen fluoride forms a salt with the amino compound.

Separately, another amino compound is added to the reaction system as an acid acceptor if necessary. Hydrogen fluoride can also form a salt with the other amino compound which is optionally added. Then, to remove the salt of hydrogen fluoride with amino compound (hydrofluoric acid amine salt, hereinafter) from within the reaction system and isolate the target amide compound, post-treatment by water washing is generally carried out.

However, some amide compounds produced are not effectively separable from water. Then the prior direct reaction process has the problems that time-consuming many steps are necessary until the target amide compound is obtained, and incomplete purification allows a large amount of hydrofluoric acid amine salt to remain in the amide compound product, which eventually invites a decline of production yield. Even with a target amide compound that can be isolated by distillation, if the removal of hydrofluoric acid amine salt in the preceding step is incomplete, the hydrofluoric acid amine salt will sublimate during the distillation step so that the distilled fraction is contaminated with it. Sometimes, the hydrofluoric acid amine salt will precipitate on a cooling section of a distillation column, clogging the distillation column.

As a means of avoiding these problems, Japanese Patent No. 2,855,081 discloses to add a silazane compound to a reaction mixture resulting from reaction of a compound having an acyl fluoride group within a molecule with an amino compound and containing the amide compound and hydrogen fluoride and/or a salt of hydrogen fluoride with the amino compound, for thereby removing the hydrogen fluoride and/or the salt of hydrogen fluoride with the amino compound.

Although this method is superior to the previous water washing method, it is difficult to remove unreacted silazane compound and partially reacted silazane compounds remaining in the system at the end of reaction, which mostly cause the target amide compound to be colored. The silazane compound used in this method is generally expensive and sensitive to air-borne moisture and thus difficult to handle.

It would be desirable to have an amide compound purifying method capable of recovering an amide compound, from a reaction mixture resulting from reaction of an acyl fluoride group-bearing compound with an amino compound, through simple steps and in a high yield and high purity.

SUMMARY OF THE INVENTION

An object of the invention is to provide an amide compound purifying method capable of recovering an amide compound in high purity form, from a reaction mixture resulting from reaction of an acyl fluoride group-bearing compound with an amino compound, through simple steps and in a high yield.

The invention pertains to a reaction mixture resulting from reaction of an acyl fluoride group-bearing compound with an amino compound and containing the amide compound and a hydrofluoric acid amine salt. The inventors have found that when an oxide, carbonate or hydroxide of an alkaline earth metal is to the reaction mixture, the alkaline earth metal compound reacts with the fluoride ion of the hydrofluoric acid amine salt to form an alkaline earth metal fluoride salt that can be readily removed by filtration. Since the hydrofluoric acid amine salt is extinguished, the post-treatment is simplified. Through the very simple procedure, the target amide compound is recovered in high purity form and in high yields.

The present invention provides a method for purifying an amide compound by adding an oxide, carbonate or hydroxide of an alkaline earth metal or a mixture thereof to a reaction mixture resulting from reaction of a compound having an acyl fluoride group within a molecule with an amino compound and containing the amide compound and hydrogen fluoride and/or a salt of hydrogen fluoride with the amino compound, and removing the hydrogen fluoride and/or the hydrogen fluoride-amino compound salt from the reaction mixture. The alkaline earth metal is most preferably calcium.

DESCRIPTION OF THE PREFERRED EMBODIMENTS

When an amide compound is synthesized through reaction of a compound having an acyl fluoride group within a molecule with an amino compound in the presence or absence of a solvent by a per se known process, there results a reaction mixture to be managed by the present invention. This reaction mixture contains, for example, the target amide compound and by-products including hydrogen fluoride and/or a hydrofluoric acid amine salt resulting from reaction of hydrogen fluoride with an excess of the amino compound, which are produced according to the following reaction formulae (A) and (B).

$$—COF+ =NH \to —CON= +HF \tag{A}$$

$$=NH+HF \to =N^+H_2F^- \tag{B}$$

Where a tertiary amino compound which is non-reactive with the acyl fluoride group and unable to produce an amide compound is present in a reaction system as an acid acceptor, hydrogen fluoride by-product reacts with the tertiary amino compound to form a hydrofluoric acid amine salt as well.

As used herein, the compound having an acyl fluoride group within a molecule refers to a compound having one or more acyl fluoride groups per molecule. Suitable compounds are those of the following general formulae, but not limited thereto.

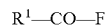

$R^1$—CO—F

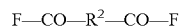

F—CO—$R^2$—CO—F

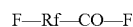

F—Rf—CO—F

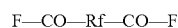

F—CO—Rf—CO—F

Herein, $R^1$ is a monovalent hydrocarbon group having 1 to 20 carbon atoms, preferably 1 to 10 carbon atoms. Examples include alkyl groups such as methyl, ethyl, propyl, isopropyl, butyl, isobutyl, tert-butyl, pentyl, neopentyl, hexyl, cyclohexyl, heptyl, octyl, nonyl, decyl, undecyl, dodecyl, tridecyl, pentadecyl, and heptadecyl, and aryl groups such as phenyl, tolyl, xylyl, naphthyl, biphenyl, and trifluoromethylphenyl.

$R^2$ is a divalent hydrocarbon group having 1 to 20 carbon atoms, preferably 1 to 10 carbon atoms. Examples include alkylene groups such as methylene, ethylene, propylene, tetramethylene, hexamethylene, methylethylene, methylpropylene, and octamethylene, and arylene groups such as phenylene, tolylene, xylylene, naphthylene, biphenylene, and trifluoromethylphenylene, and combinations of such an alkylene group with an arylene group.

Rf is a divalent perfluoroalkylene group or a perfluoroalkylene ether group having at least one ether bond oxygen atom. The structures of the perfluoroalkylene ether groups represented by Rf include those of the general formula:

$$-(Rf^1-O)_q-$$

wherein $Rf^1$ is a straight or branched perfluoroalkylene group having 1 to 6 carbon atoms, preferably 1 to 3 carbon atoms, q is an integer of 1 to 1,000, preferably 2 to 600, and more preferably 5 to 300.

Examples of the recurring units $-(Rf^1-O)-$ include $-CF_2O-$, $-CF_2CF_2O-$, $-CF_2CF_2CF_2O-$, $-CF(CF_3)CF_2O-$, $-CF_2CF_2CF_2CF_2O-$, $-CF_2CF_2CF_2CF_2CF_2O-$, and $-C(CF_3)_2O-$. Of these, $-CF_2O-$, $-CF_2CF_2O-$, $-CF_2CF_2CF_2O-$, and $-CF(CF_3)CF_2O-$ are preferred.

The perfluoroalkylene ether structure may be composed of recurring units $-(Rf^1-O)-$ of one type or a combination of two or more types.

In the event the compound has more than one acyl fluoride group within a molecule, at least one group should be an acyl fluoride group, and the remaining group(s) may have been converted to a methyl ester, ethyl ester, acrylate, methacrylate or analogous group(s).

The amino compound which reacts with the acyl fluoride group-bearing compound to form an amide compound is typically selected from ammonia, and compounds having a primary or secondary amino group within a molecule.

In the reaction system, there may be present as an acid acceptor an amino compound which is of the same type as or different type from the reactant amino compound and which will react with hydrogen fluoride in the reaction mixture to form a salt. The reactant amino compound or the amino compound as the acid acceptor is selected from ammonia and compounds having a primary, secondary or tertiary amino group within a molecule, for example, ammonia, monoalkylamines such as methylamine, ethylamine, propylamine, isopropylamine, butylamine, isobutylamine, tert-butylamine, hexylamine, octylamine, decylamine, and cyclohexylamine; monoalkenylamines such as allylamine, propenylamine, isopropenylamine and butenylamine; monoarylamines such as aniline; dialkylamines such as dimethylamine, diethylamine, methylethylamine and dibutylamine; and trialkylamines such as piperidine, piperazine, N-methylallylamine, diphenylamine, 2-aminopyridine, triethylamine, and tributylamine.

Where it is desired that the reactant amino compound also serve as the acid acceptor, the reactant amino compound may be used in stoichiometric excess relative to the acyl fluoride group-bearing compound. The compound having only a tertiary amino group is often utilized as the acid acceptor since it reacts with hydrogen fluoride to form a hydrofluoric acid amine salt, but not with the reactant, acyl fluoride group-bearing compound.

According to the invention, an oxide, carbonate or hydroxide of an alkaline earth metal or a mixture thereof is added to the reaction mixture resulting from the aforementioned process whereby the fluoride ion of hydrogen fluoride and/or hydrofluoric acid amine salt in the reaction mixture is removed as an alkaline earth metal fluoride salt.

Reaction for alkaline earth metal oxide $$2H^+F^- + MO \rightarrow MF_2 + H_2O$$

Reaction for alkaline earth metal carbonate $$2H^+F^- + MCO_3 \rightarrow MF_2 + CO_2 + H_2O$$

Reaction for alkaline earth metal hydroxide $$2H^+F^- + M(OH)_2 \rightarrow MF_2 + 2H_2O$$

Herein, M is an alkaline earth metal.

The products of these reactions include the alkaline earth metal fluoride salt, water and carbon dioxide gas. The unreacted oxide, carbonate or hydroxide of alkaline earth metal and the alkaline earth metal fluoride can be removed simply by filtration. Water is produced in a relatively small amount, which can be readily removed. No extra removal operation is necessary for carbon dioxide gas because it is usually released during the reaction.

The method for the purification of amide compound through fluoride ion salt-forming treatment of hydrogen fluoride and/or hydrofluoric acid amine salt entails by-products which are all readily removable in this way. Then the post-treatment following amidation is simplified and the content of impurities, especially fluoride ion components, in the target amide compound is minimized.

The oxide, carbonate or hydroxide of alkaline earth metal which can be used herein may be any desired one as long as it reacts with hydrogen fluoride and/or hydrofluoric acid amine salt to form an alkaline earth metal fluoride salt. Examples include magnesium carbonate, magnesium oxide, magnesium hydroxide, calcium carbonate, calcium oxide and calcium hydroxide. Of these, calcium carbonate, calcium oxide and calcium hydroxide are preferred because of easier removal of their reaction products, with calcium carbonate being most preferred. The oxide, carbonate or hydroxide of alkaline earth metal may be used alone or in admixture of two or more. A natural material containing them in a suitable proportion is also useful as purchased or in a milled or processed form.

Preferably the amount of the alkaline earth metal oxide, carbonate or hydroxide used is adjusted so as to give an amount of alkaline earth atoms in reactive form which is 0.49 to 4 times, especially 0.6 to 2 times, on a molar basis, the stoichiometry of fluoride ions contained in the hydrogen fluoride and/or hydrofluoric acid amine salt formed during the amidation reaction. Effective reaction takes place even under conditions where alkaline earth atoms are present in more excess.

For the inventive reaction of the alkaline earth metal compound with fluoride ions of the hydrogen fluoride and/or hydrofluoric acid amine salt formed during the amidation reaction, no particular limit is imposed on the reaction temperature as long as an alkaline earth metal fluoride salt can be formed. Preferably the reaction temperature is 0 to 200° C., more preferably 10 to 160° C. The completion of reaction can be ascertained by monitoring the concentration of water-soluble fluoride ions in the solution or the ceasing of formation of reaction products (to be removed). When a carbonate is used, for example, the completion is ascertained by the ceased evolution of carbon dioxide gas.

A solvent is not necessarily needed in the inventive reaction although aprotic polar solvents such as toluene, hexane, tetrahydrofuran and glymes, which have no negative impact on the inventive reaction, may be used at any stage and if desired.

EXAMPLE

Examples of the invention are given below by way of illustration and not by way of limitation.

Example 1

In a flask, 300 g (—COF group, 0.102 mol) of a difunctional acyl fluoride compound of formula (1) below and 30 g of hexafluoro-meta-xylene were mixed by agitation under a nitrogen atmosphere.

Thereafter, 10.23 g (0.102 mol) of calcium carbonate was added to the reaction mixture. With stirring, the system was heated up to 100° C. over 30 minutes. It was confirmed that carbon dioxide gas evolved as the temperature of the system rose. Agitation was continued at 100° C. for 30 minutes. After it was confirmed that the gas evolution ceased completely, the solvent and low-boiling fractions were distilled off under vacuum conditions of 160° C./2 mmHg over 4 hours.

The reaction mixture which had been stripped of the solvent and low-boiling fractions was cooled to room temperature, diluted with 150 g of a fluorocarbon solvent FC-77 (3M) and filtered. The filtrate was stripped of the solvent FC-77 at 130° C./2 mmHg, whereupon 305 g (yield 96%) of a pale yellow colored clear liquid (Hazen unit 100) was recovered. On analysis by $^1$H-NMR, $^{19}$F-NMR and IR, the liquid was identified to be an amide compound of the following formula (3).

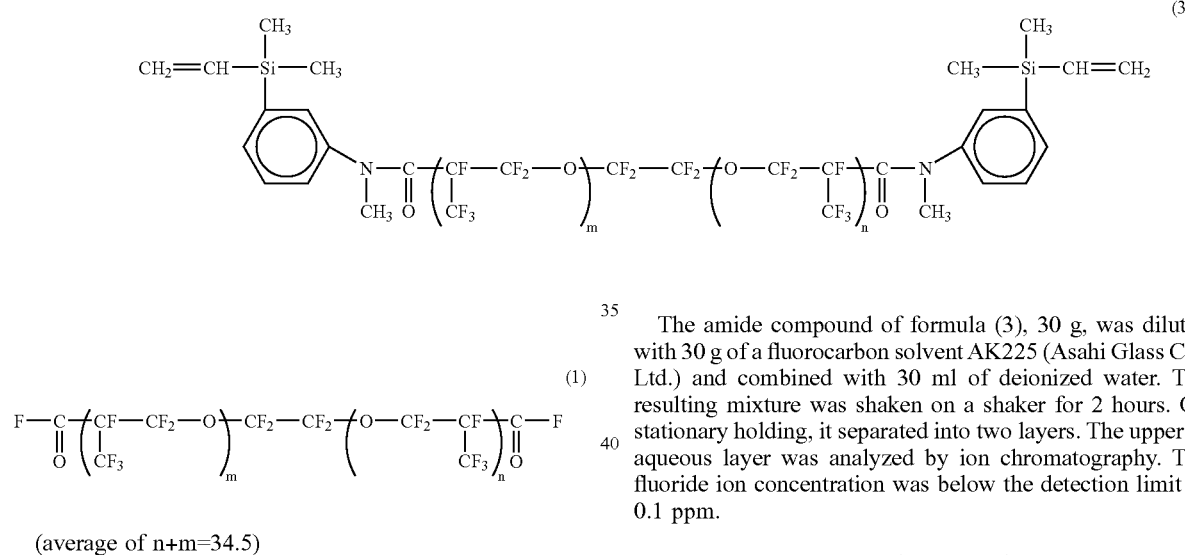

(average of n+m=34.5)

From a dropping funnel, a mixture of 23.5 g (0.123 mol) of an amine compound of formula (2) below and 12.4 g (0.123 mol) of triethylamine was added to the flask dropwise over 20 minutes.

During the dropwise addition, the temperature within the flask rose from 22° C. to 37° C. and the system turned pale yellow and turbid due to formation of a hydrofluoric acid amine salt. After the completion of dropwise addition, the flask was heated until the internal temperature reached 60° C., at which the contents were agitated for a further one hour.

The amide compound of formula (3), 30 g, was diluted with 30 g of a fluorocarbon solvent AK225 (Asahi Glass Co., Ltd.) and combined with 30 ml of deionized water. The resulting mixture was shaken on a shaker for 2 hours. On stationary holding, it separated into two layers. The upper or aqueous layer was analyzed by ion chromatography. The fluoride ion concentration was below the detection limit of 0.1 ppm.

Comparative Example 1

The same procedure as in Example 1 was repeated until a mixture of the difunctional acyl fluoride compound of formula (1) with the amine compound of formula (2) and triethylamine was agitated at 60° C. for one hour. Thereafter, 17.80 g (0.102 mol) of diethylaminotrimethylsilane was added to the reaction mixture. The system was agitated at 60° C. for one hour. The system was then heated up to 100° C., followed by agitation for one hour. The solvent and low-boiling fractions were distilled off under vacuum conditions of 160° C./2 mmHg over 4 hours.

The reaction mixture which had been stripped of the solvent and low-boiling fractions was cooled to room temperature, diluted with 150 g of a fluorocarbon solvent FC-77 (3M) and filtered. The filtrate was stripped of the solvent FC-77 at 130° C./2 mmHg, whereupon 303 g (yield 95%) of a brown colored liquid (Hazen unit >500) was recovered. On analysis by $^1$H-NMR, $^{19}$F-NMR and IR, the liquid was identified to be an amide compound of the above formula (3).

The amide compound of formula (3), 30 g, was diluted with 30 g of a fluorocarbon solvent AK225 (Asahi Glass Co., Ltd.) and combined with 30 ml of deionized water. The resulting mixture was shaken on a shaker for 2 hours. On stationary holding, it separated into two layers. The upper or aqueous layer was analyzed by ion chromatography. The fluoride ion concentration was 3.2 ppm.

According to the invention, by-products, hydrogen fluoride and hydrofluoric acid amine salt in the amidation reaction system can be briefly treated and removed in a simple way. This prevents the amide compound from being colored with by-products and simplifies the purification step following amidation. Then the target amide compound having a high purity, i.e., a minimal concentration of fluoride ions is recovered in high yields.

Japanese Patent Application No. 2003-119375 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for purifying an amide compound comprising adding an oxide, carbonate or hydroxide of an alkaline earth metal or a mixture thereof to a reaction mixture resulting from reaction of a compound having at least one acyl fluoride group with an amino compound, and containing the amide compound and hydrogen fluoride and/or a salt of hydrogen fluoride with the amino compound, and removing the hydrogen fluoride and/or the salt of hydrogen fluoride with the amino compound from the reaction mixture.

2. The method of claim 1 wherein said alkaline earth metal is calcium.

3. The method of claim 1 wherein the amino compound is ammonia, or a primary or secondary amine.

4. The method of claim 1 wherein a tertiary amino compound which is non-reactive with the acyl fluoride group and unable to produce an amide compound is present in the reaction mixture as an acid acceptor.

5. The method of claim 1 wherein the compound having at least one acyl fluoride group is at least one selected from the group consisting of $R^1$—CO—F, F—CO—$R^2$—CO—F, F—Rf—CO—F, and F—CO—Rf—CO—F, wherein $R^1$ is a monovalent hydrocarbon group having 1 to 20 carbon atoms, $R^2$ is a divalent hydrocarbon group having 1 to 20 carbon atoms, and Rf is a divalent perfluoroalkylene group or a perfluoroalkylene ether group having at least one ether bond oxygen atom.

6. The method of claim 5 wherein the compound contains an Rf group, and Rf is said perfluoroalkylene ether group having at least one ether bond oxygen atom, and has the general formula:

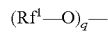

wherein $Rf^1$ is a straight or branched perfluoroalkylene group having 1 to 6 carbon atoms, and q is an integer of 1 to 1,000, and when q is greater than 1, the recurring units —($Rf^1$—O)— may be the same or different.

7. The method of claim 1 wherein the amount of the oxide, carbonate or hydroxide of an alkaline earth metal provides an amount of alkaline earth atoms in reactive form which is 0.49 to 4 times, on a molar basis, the stoichiometry of fluoride ions contained in the hydrogen fluoride and/or the salt of hydrogen fluoride with the amino compound formed during the reaction.

8. The method of claim 1 wherein the compound having at least one acyl fluoride has the following formula (1):

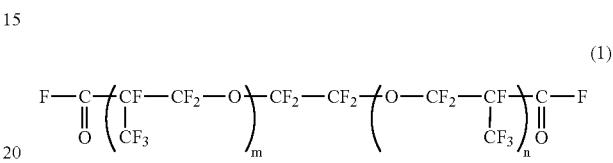

(average of n+m=34.5), the amino compound includes one having the following formula (2):

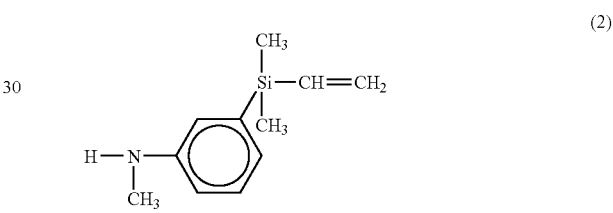

and the amide compound has the following formula (3):

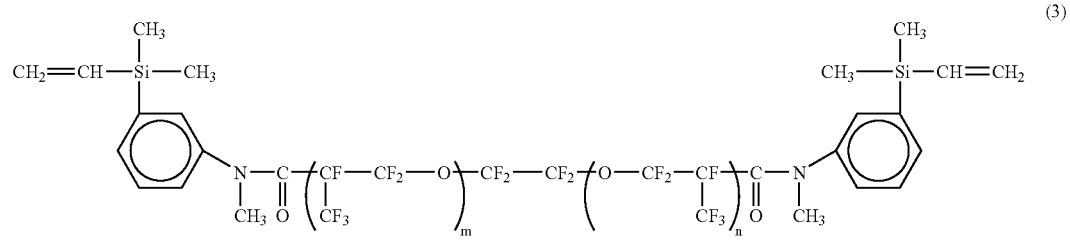

9. The method of claim 1 wherein the reaction mixture contains said salt of hydrogen fluoride with the amino compound.

10. The method of claim 9 wherein said alkaline earth metal is calcium.

11. The method of claim 9 wherein the amino compound is ammonia, or a primary or secondary amine.

12. The method of claim 9 wherein a tertiary amino compound which is non-reactive with the acyl fluoride group and unable to produce an amide compound is present in the reaction mixture as an acid acceptor.

13. The method of claim 9 wherein the compound having at least one acyl fluoride group is at least one selected from the group consisting of $R^1$—CO—F, F—CO—$R^2$—CO—F, F—Rf—CO—F, and F—CO—Rf—CO—F, wherein $R^1$ is a monovalent hydrocarbon group having 1 to 20 carbon atoms, $R^2$ is a divalent hydrocarbon group having 1 to 20 carbon atoms, and Rf is a divalent perfluoroalkylene group or a perfluoroalkylene ether group having at least one ether bond oxygen atom.

14. The method of claim 13 wherein the compound contains an Rf group, and Rf is said perfluoroalkylene ether group having at least one ether bond oxygen atom, and has the general formula:

$$-(Rf^1-O)_q-$$

wherein $Rf^1$ is a straight or branched perfluoroalkylene group having 1 to 6 carbon atoms, and q is an integer of 1 to 1,000, and when q is greater than 1, the recurring units $-(Rf^1-O)-$ may be the same or different.

15. The method of claim 9 wherein the amount of the oxide, carbonate or hydroxide of an alkaline earth metal provides an amount of alkaline earth atoms in reactive form which is 0.49 to 4 times, on a molar basis, the stoichiometry of fluoride ions contained in the hydrogen fluoride and/or the salt of hydrogen fluoride with the amino compound formed during the reaction.

16. The method of claim 9 wherein the compound having at least one acyl fluoride has the following formula (1):

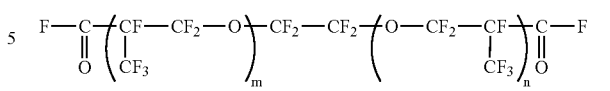

(average of n+m=34.5), the amino compound includes one having the following formula (2):

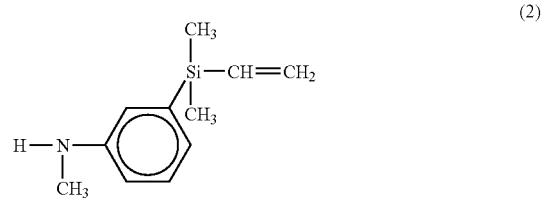

and the amide compound has the following formula (3):

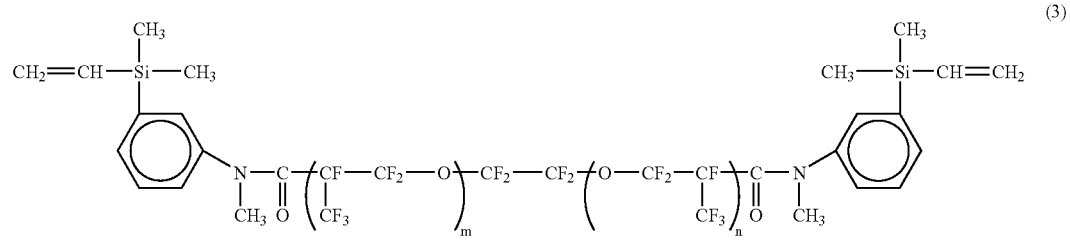

* * * * *